United States Patent
Anthony et al.

(10) Patent No.: US 6,377,340 B1
(45) Date of Patent: Apr. 23, 2002

(54) METHOD OF DETECTION OF NATURAL DIAMONDS THAT HAVE BEEN PROCESSED AT HIGH PRESSURE AND HIGH TEMPERATURES

(75) Inventors: Thomas Richard Anthony, Niskayuna, NY (US); John Kieran Casey; Alan Cameron Smith, both of Dublin (IE); Suresh Shankarappa Vagarali, Columbus, OH (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/430,477

(22) Filed: Oct. 29, 1999

(51) Int. Cl.$^7$ ............................................. G01N 21/00

(52) U.S. Cl. .................... 356/30; 356/244; 250/372; 250/330

(58) Field of Search ................. 356/30, 244; 250/461.1, 250/461.2, 458.1, 459.1, 559.4, 330, 372; 209/577–579, 589; 423/446; 372/41–42

(56) References Cited

U.S. PATENT DOCUMENTS

| | | | |
|---|---|---|---|
| 4,638,484 A | * 1/1987 | Rand et al. | 372/42 |
| 4,880,613 A | * 11/1989 | Satoh et al. | 423/446 |
| 5,118,181 A | * 6/1992 | Yifrach et al. | 356/30 |
| 5,385,762 A | * 1/1995 | Prins | 427/526 |
| 5,420,879 A | * 5/1995 | Kawarada et al. | 372/41 |
| 5,536,943 A | * 7/1996 | Smith et al. | 250/372 |
| 5,628,824 A | * 5/1997 | Vohra et al. | 423/446 |
| 5,801,819 A | * 9/1998 | Spear et al. | 356/30 |
| 5,811,817 A | * 9/1998 | Ravich | 356/30 |
| 5,835,200 A | * 11/1998 | Smith et al. | 356/30 |
| 5,883,388 A | * 3/1999 | Smith et al. | 250/330 |
| 5,883,389 A | * 3/1999 | Spear et al. | 250/461.1 |

FOREIGN PATENT DOCUMENTS

GB 2303699 * 2/1997

OTHER PUBLICATIONS

XP–000979984, Christopher P. Smith et al., "GE POL Diamonds: Before and After", Gems & Gemology, pp. 192–215, Sep. 2000.

XP–000980582, Peter R. Buerki et al., "Observation of the H2 Defect in Gem–Quality Type Ia Diamond", Diamond and Related Materials, vol. 8, pp. 1061–1066, 1999.

XP 002159681, Simon C. Lawson et al., "Spectroscopic Study of Cobalt–Related Optical Centers in Synthetic Diamond", Journal of Applied Physics, vol. 79, No. 8, pp. 4348–4357, Apr. 15, 1996.

XP–000965245, M. R. Brozel et al., "Partial Dissociation of Nitrogen Aggregates in Diamond By high Temperature–High Pressure Treatments", proc. Royal Society London, vol. A 361, pp. 109–127, 1978.

XP–000710884, A. T. Collins, *A Spectroscopic Survey of Naturally–Occurring Vacancy–Related Colour Centres in Diamond*, Journal of Physics D. Applied Physics, vol. 15, pp. 1431–1438, 1982.

* cited by examiner

*Primary Examiner*—Frank G. Font
*Assistant Examiner*—Sang H. Nguyen
(74) *Attorney, Agent, or Firm*—Robert Santandrea; Noreen C. Johnson

(57) ABSTRACT

A method for detecting whether a natural diamond has been processed at high pressure and high temperature (HPHT) conditions comprises steps of disposing the diamond in a cyrostat that is provided at temperatures equal to or less than liquid nitrogen; illuminating the diamond with a laser beam; recording an optical spectrum of the diamond with a photoluminescence spectrometer; and examining the optical spectrum of the diamond to detect an absence of selected photoluminescent spectral lines. The invention also sets forth a method for predicting whether a natural diamond has been treated under HPHT conditions

69 Claims, 4 Drawing Sheets

METHOD OF DETECTION OF NATURAL DIAMONDS THAT HAVE BEEN PROCESSED AT HIGH PRESSURE AND HIGH TEMPERATURES

BACKGROUND OF THE INVENTION

The file of this patent contains at least one drawing executed in color. Copies of this patent with color drawings will be provided by the Patent and Trademark Office upon request and payment of the necessary fee.

The invention relates to a method for detecting processed gem-quality colorless and fancy-colored diamonds. In particular, the invention relates to a method for detecting processed diamonds that have been produced from inferior-grade discolored diamonds by a high-temperature and high-pressure (HPHT) process.

Diamonds are conventionally divided into four main categories, which are designated as Type Ia, Type Ib, Type IIa, and Type IIb. In reality, there is a smooth change in impurity concentration/arrangement between the four types so that intermediate varieties thereof also exist.

Type I diamonds contain nitrogen as the major impurity, and can be divided into Type Ia diamonds and Type Ib diamonds. Type Ia diamonds contain a nitrogen impurity that exists in an agglomerated state. The agglomerated state exists as nitrogen pairs, called "A Centers" (Type IaA), nitrogen clusters comprising four nitrogen atoms called "B centers" (Type IaB), and mixtures thereof (Type IaA/B). Type Ib diamonds contain nitrogen as isolated single nitrogen atoms called "C Centers". Some Type I diamonds may also contain clusters of three nitrogen atoms called "N3 Centers".

Type Ia diamonds comprise over about 98% of the larger clear natural diamonds. Type Ib diamonds are rarer and amount to only about 0.8% of natural diamonds. Type Ia diamonds may also contain platelets, which are small flat inclusions that a few atoms thick and about 300 atoms across. The platelets may contain some nitrogen in an unspecified form. Type Ia diamonds also may contain voidites, which are small equiaxed cavities that are either vacant or that contain nitrogen in an unspecified form. Voidites tend to typically exist in Type IaA/B diamonds or Type IaB diamonds.

Natural diamonds may possess a color that can range from clear and colorless diamonds to yellow, orange, red, pink, blue, brown, and even green colored diamonds. Intermediate colored diamonds are also possible. Diamonds can even appear to change color depending on the lighting conditions. These diamonds are known in the art as "chameleon" diamonds. For natural diamonds, a brownish color is the most common, and may occur in up to about 98% of mined natural diamonds. The brownish and pinkish color is believed to be a result of plastic deformation of the diamonds after they were formed.

Most natural Type Ia diamonds have a brownish color. A brownish color may result from a mixture of many other colors. For example, the brownish color may result from a mixture of yellowish coloring (such as from isolated nitrogen atoms (C Centers) or N3 centers) with some blackish coloring (such as from submicroscopic inclusions of graphite). The mixture of yellowish and blackish colorings will produce a brownish color. Further, a brownish coloring in a diamond can be formed from a mixture of color centers that produce a greenish coloring in a diamond with a color center that produces a reddish coloring in a diamond. An infinite number of color combinations that produce a brownish color is possible. Therefore, it is generally impossible to determine the color centers causing the color of a diamond by its color alone.

Type II diamonds are conventionally defined as diamonds that contain less than 1 PPM of nitrogen. The selection of 1 PPM nitrogen level is historically related to the fact that this was the level of nitrogen routinely detectable in infrared spectrums of gem diamonds. Type II diamonds are further divided into Type IIa and Type IIb. Type IIa diamonds have no other impurities other than nitrogen at less than a 1 PPM level. Type II diamonds contain boron in the parts per million range and the boron concentration always exceed any nitrogen concentration in the crystal. Type IIb diamonds are blue in color and are extremely rare, and thus have a high value per carat as jewelry items.

The pricing of diamonds typically is a function of their color. Diamonds that exhibit fancy colors, such as the canary yellows, blues, reds, pinks, and greens, are rare and tend to have the highest prices. Diamonds that are classified as "colorless diamonds" command the highest prices after fancy colored diamonds. The degree of colorlessness lends to a nonlinear price effect of the diamond. Even the faintest tinge of yellow can considerably reduce the price of colorless diamonds. Brownish diamonds are an exception to the above-stated fancy color diamond market, as they are very common. Brownish diamonds typically have been culled and used as industrial diamonds, and thus the brownish diamonds are relatively inexpensive.

An aesthetic and economic incentive thus exists to change relatively inexpensive brownish colored diamonds to either of the more valuable colorless diamonds or to fancy color diamonds in view of the relative scarcity and beauty of fancy colors, colorless, and the commonality of brownish diamonds. Various methods have been proposed and used to treat diamonds. For example, irradiation has been used to change the diamond color from typically unattractive off-colors to attractive blue, green, orange, black, and yellow colors. Also, electrons, neutrons, gamma rays, and alpha particles have been proposed and used to produce irradiation-produced color centers in diamonds. Neutron, gamma, and electron irradiation have been generally used because these methods produce a more uniform coloration in diamonds due to an effective penetrating power into the diamonds. However, neutrons used for treating diamonds may introduce dangerous side effects since radioactive species can be produced in diamond inclusions by neutron activation. Additionally, typical electron or alpha irradiation methods merely develop a superficial color that is confined to outer portions of the diamonds.

Further, methods such as, but not limited to, laser-drilling, fracture-filling, and surface-coating have been proposed and used to treat diamonds in attempts to increase their value. These methods, while somewhat effective in the color change, are easily detected by conventional gemological practices. For example, an observation of diamonds in an optical microscope may reveal treating by laser-drilling, fracture-filling, and surface-coating methods.

Most diamond treating is easily detected by looking at infrared and optical spectrums of the diamonds. The treating produces infrared and optical spectrum characteristics (also known as "detection signatures"), which include detectable different radiations that are produced by vacancies in diamonds. The detection signatures or optical spectra signature characteristics are observed in the GR1 band of the visible spectrum; and absorption at 740.9 nm and from 412–430 nm by the GR1 band that produces a green, blue-green, dark green, or even a black color in the diamond by absorption.

Vacancy color centers introduced by irradiation may be modified by high-temperature annealing treatments to produce diamond colors that range from blue to pinkish to red to green colors. Annealing can be conducted at temperatures as low as about 600° C., because the large number of vacancies introduced by irradiation temporarily increases the mobility of nitrogen and other impurities in the diamonds. During the annealing, the vacancies diffuse to, and are absorbed by at least one of vacancy sinks in the diamond, such as, but not limited to, free surfaces, dislocations, and inclusion interfaces, and complexes of nitrogen, such as A, B, and C Centers in the diamonds. As the vacancies disappear, their immediate influence on the observed diamond color lessens. Thus, the diamond color gradually changes from blue to green to brownish to yellow and back to the original color of the diamond. The annealing can be stopped at any point during the annealing to produce a desired treated diamond color. Multiple irradiation steps and annealing steps may be conducted to manipulate and change the treated diamond color.

Recently, attempts to treat diamonds by annealing them at progressively higher temperatures to eliminate indications of irradiation, for example optical spectra signature characteristics. For example, the GR1 line that results from a vacancy formed during irradiation treatment begins to disappear above 400° C. as the vacancies anneal out of the diamond crystal. Other irradiation lines, however, persist to higher temperatures. Conventional color change treatments for diamonds may produce color changes therein; however the material and mechanical properties and characteristics of the diamonds are often impaired. The elimination of any indications of irradiation in diamonds is desired because "treated" diamonds have a discounted value with respect to natural diamonds.

Electron or neutron irradiation of Type Ia diamonds and a subsequent heat treatment generates H3 (Nitrogen-Vacancy-Nitrogen) centers and H4 (Nitrogen-Nitrogen-Vacancy-Nitrogen-Nitrogen) centers therein. These centers provide an amber gold color to the treated diamonds. The H3 centers and H4 Centers, respectively, have absorption bands at 503 nm and 496 nm, which are characteristic optical spectra signatures of these treated Type Ia diamonds. The ratios of H3 centers to H4 centers and the ratio of A centers to B centers in the diamonds can distinguish natural diamonds from these irradiation and annealed treated diamonds.

Further, a vacancy in a diamond can combine with a single nitrogen C Center and form an H2 Center (Nitrogen-Vacancy). The H2 Center can impart a distinguishable optical spectra signature characteristic of treated diamonds. The H2 Center can cause a greenish color in the diamonds and its optical spectra signature characteristic is a vibronic absorption band at 637.3 nm. By absorbing light in the red at 637 nm, the remaining light coming from these treated diamonds is shifted towards a greenish color, and thus a detectable spectra signature characteristic for these treated diamonds is evident and apparent.

Recently, processing has improved a diamond's color, such as by exposing the diamonds to high-pressure high-temperature (HPHT) conditions, which attempt to simulate those conditions in the earth's mantle. Many of these color-improved diamonds are Type I diamonds with low nitrogen concentrations or Type II diamonds with nominally no nitrogen. Conventional analyzing of these color-improved diamonds has not been able to discern that they have been processed. It is believed that the analyzing fails because of: the low concentration or lack of nitrogen; measurements of A, B, and C Center concentrations, measurements of H2, H3 and H4 center concentrations, measurements of optical and infrared spectral signatures associated with nitrogen, nitrogen complexes, vacancies and vacancy-nitrogen pairs, or vacancy-nitrogen-complex agglomerates are not able to determine whether the diamond has been exposed to HPHT processing.

Therefore, a method for determining the existence of a processed diamonds is needed.

SUMMARY OF THE INVENTION

The invention sets forth a method for detecting whether a natural diamond has been processed at high pressure and high temperature (HPHT) conditions. The method comprises steps of disposing the diamond in a cryostat that is provided at temperatures equal to or less than liquid nitrogen; illuminating the diamond with a laser beam; recording an optical spectrum of the diamond with a photoluminescence spectrometer; and examining the optical spectrum of the diamond to detect an absence of selected photoluminescent spectral lines.

The invention also sets forth a method for predicting whether a natural diamond has been processed at high pressure and high temperature (HPHT) conditions. The prediction method comprises steps of disposing a diamond in a cryostat that is provided at temperatures equal to or less than liquid nitrogen; illuminating the diamond with a laser beam; recording an optical spectrum of the diamond with a photoluminescence spectrometer; examining the optical spectrum of the diamond to detect an absence of selected photoluminescent spectral lines; and predicting that the diamond has been treated if at least one of selected photoluminescent spectral lines is not in the optical spectrum.

Further, the invention also sets forth a method for detecting whether a natural diamond has been processed at high pressure and high temperature (HPHT) conditions. This method comprises steps of disposing the diamond in a cryostat that is provided at temperatures equal to or less than liquid nitrogen; illuminating the diamond with a laser beam; recording an optical spectrum of the diamond with a photoluminescence spectrometer; and examining the optical spectrum of the diamond to detect an absence of a spectral line at 2.53 eV. If the 2.53 eV spectral line is not present in the optical spectrum, the method determines with up to about a 95% probability exists that the diamond was processed under HPHT conditions, and if the 2.53 eV spectral line is present, the method determines that the diamond has not been subjected to HPHT conditions.

Another aspect of the invention, sets forth a method for predicting whether a natural diamond has been processed at high pressure and high temperature (HPHT) conditions. This prediction method comprises steps of disposing a diamond in a cyrostat that is provided at temperatures equal to or less than liquid nitrogen; illuminating the diamond with a laser beam; recording an optical spectrum of the diamond with a photoluminescence spectrometer; examining the optical spectrum of the diamond to detect an absence of spectral lines at 2.53 eV; and predicting that the diamond has been treated if at least one of selected photoluminescent spectral lines is not in the optical spectrum. If the 2.53 eV spectral line is not present in the optical spectrum, the prediction method determines with up to about a 95% probability exists that the diamond was processed under HPHT conditions, and if the 2.53 eV spectral line is present, the prediction method determines that the diamond has not been subjected to HPHT conditions.

These and other aspects, advantages and salient features of the invention will become apparent from the following detailed description, which, when taken in conjunction with the annexed drawings, where like parts are designated by like reference characters throughout the drawings, disclose embodiments of the invention.

DESCRIPTION OF THE INVENTION

Figure 1:
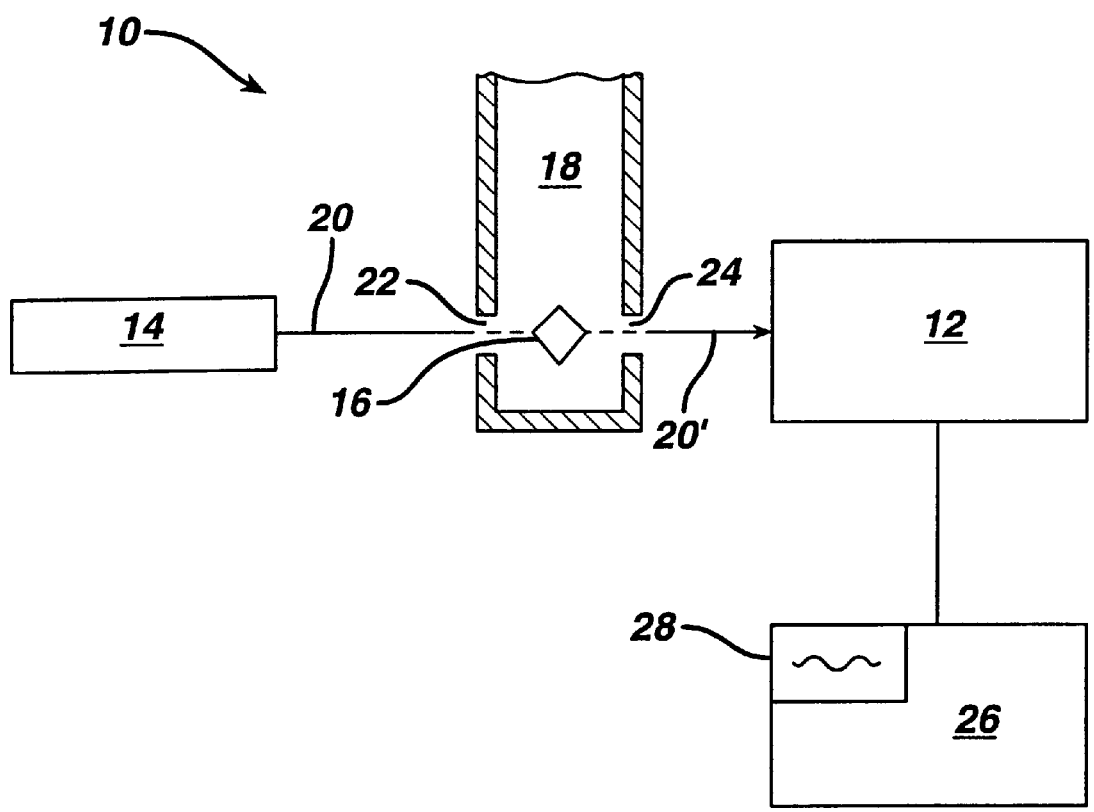
FIG. 1 is a schematic illustration of a detection system used in the method, as embodied by the invention, in which the system includes a laser excitation source, a sample diamond in a low-temperature cryostat, and a photoluminescence spectrometer.

The method, as embodied by the invention, non-destructively detects high pressure and high temperature (HPHT)-processed diamonds. The method, as embodied by the invention, also provides an ability to economically evaluate and detect HPHT-processed diamonds in a very short time, for example in times up to about 30 minutes.

A summary discussion of diamond configurations, mechanics, and other characteristics will now be provided in order to facilitate the discussion of the method and its associated system, as embodied by the invention. As discussed above, diamonds are conventionally divided into four main categories, Type Ia, Type Ib, Type IIa, and Type IIb. Type I diamonds contain nitrogen as the major impurity. Type I diamonds are divided into Type Ia diamonds and Type Ib diamonds, in which Type Ia diamonds contain a nitrogen impurity that exists in an agglomerated state. The agglomerated state exists as nitrogen pairs, called "A Centers" (Type IaA), nitrogen clusters comprising four nitrogen atoms called "B centers" (Type IaB), and mixtures thereof (Type IaA/B). Type Ib diamonds contain nitrogen as isolated single nitrogen atoms called "C Centers". Some Type I diamonds may also contain clusters of three nitrogen atoms called "N3 Centers". Type Ia diamonds comprise over about 98% of the larger clear natural diamonds. Type Ib diamonds are rarer and amount to only about 0.8% of natural diamonds. Type Ia diamonds may also contain platelets, which are small flat inclusions that a few atoms thick and about 300 atoms across. The platelets may contain some nitrogen in an unspecified form. Type Ia diamonds also may contain voidites, which are small equiaxed cavities that are either vacant or that contain nitrogen in an unspecified form. Voidites tend to typically exist in Type IaA/B diamonds or Type IaB diamonds.

Natural diamonds may possess a color that can range from clear and colorless diamonds to yellow, orange, red, blue, brown, pinkish and even green colored diamonds. Intermediate colored diamonds are also possible. Diamonds can even appear to change color depending on the lighting conditions, and these diamonds are known as "chameleon" diamonds. For natural diamonds, a brownish color is the most common, and may occur in up to about 98% of mined natural diamonds. The brownish color is believed to be a result of plastic deformation of the diamonds after they were formed.

Most natural Type Ia diamonds have a brownish color. A brownish color may result from a mixture of many other colors. For example, the brownish color may result from a mixture of yellowish color-ing (such as from isolated nitrogen atoms (C Centers) or N3 centers) with some blackish color-ing (such as from submicroscopic inclusions of graphite). The mixture of yellowish and blackish color-ings will produce a brownish color. Further, a brownish color-ing in a diamond can be formed from a mixture of color centers that produce a greenish color-ing in a diamond with a color center that produces a reddish color-ing in a diamond. An infinite number of color combinations that produce a brownish color is possible Therefore, it is generally impossible to determine the color centers causing the color of a diamond by its color alone.

Type IIb diamonds may exhibit a blue color, which can be imparted by the boron impurity. Type IIb diamonds have a high value per carat as jewelry items because Type Ib diamonds are rare and their blue color has been desirable as an attractive color.

It is believed that nitrogen-containing diamonds originally are formed as Type Ib diamonds having isolated nitrogen atoms (C Centers), which were incorporated during crystal growth. The diamonds were annealed within earth's mantel at temperatures between about 1000° C. and about 1300° C. and at high pressures over a long period of time, perhaps up to 1 billion years. During this time, the nitrogen atoms migrated and principally formed two types of aggregates, pairs (A Centers) and clusters of four (B Centers).

The clusters of four nitrogen atoms (B Centers) are believed to be formed when migrating nitrogen pairs (A Centers) collide with each other. Therefore, a progression of diamonds development is believed to be from Type Ib diamonds to Type IaA diamonds to Type IaA/B diamonds to Type IaB diamonds. A small amount of nitrogen may also agglomerate and form N3 centers, which are a generally planar array of three nitrogen atoms that surround a common vacancy. It is believed that such centers are formed when isolated nitrogen (C Center) combines with a nitrogen pair (A Center) during an agglomeration process. The N3 centers apparently are less stable than A centers and B centers, as their concentration in Type Ia diamonds is relatively small. Platelets may form when the annealing has progressed to the Type IaA stage. Voidite formation, as well as some platelet disintegration, occurs as B clusters form and becomes pronounced in the Type IaB stage of annealing.

Type II diamonds are typically defined as diamonds that contain less than 1 PPM of nitrogen. Type II diamonds are further divided into Type IIa and Type IIb, in which Type IIa diamonds exhibit no other impurities other than nitrogen at levels less than a 1 PPM. Type IIb diamonds contain boron in a parts per million level range, however the boron concentration always exceeds the nitrogen concentration in the diamonds.

Diamonds exhibit atomic and line defects that are generated along slip planes. The defects are believed to be formed during plastic deformation. The slip planes act as color centers and can produce at least one of a brownish color or a pinkish color. Brownish diamonds is the most common color for diamonds while a pinkish color is very rare in diamonds. If slip planes are evenly distributed, the color of the crystal will be generally uniform. If the slip is concentrated in zones, the diamonds will exhibit an uneven color distribution with the color concentrated in inhomogeneous slip bands.

It has been discovered that brownish or pinkish color centers in diamonds can be eliminated by a high-pressure high temperature (HPHT) process at temperatures exceeding about 1000° C. and pressures that are greater than about 40 kilobars. The resulting diamonds, which are formed by the HPHT processing are generally clear and colorless. These diamonds have a color grade that can range as high as "D" on the color scale of the Gemological Institute of America (GIA), which ranges from D (completely colorless) to Z (distinctly yellow).

Type Ia diamonds containing nitrogen may be categorized as colorless if all nitrogen is in A centers or B centers in the diamonds. If isolated nitrogen atoms (C Centers) or N3 centers are present in the diamonds, the diamonds may have a yellowish color (also known in the art as "tinge"), in which the diamonds' color depends on concentrations of nitrogen atoms. Typically, N3 centers produce a washed-out yellowish color that is referred to in the art as "Cape Yellow", while isolated nitrogen atoms (C Centers) produce a richer more vibrant "Canary Yellow" color if the nitrogen atoms' concentration is sufficiently high. "Canary Yellow" diamonds are generally more valuable than "Cape Yellow" diamonds.

Changing the N3 center concentration will change the yellow color of a diamond, and may increase the overall "brilliance" or amount of light thrown back by a diamond. Electrons that are around an N3 center can absorb light in the ultraviolet part of the spectrum, as well as blue light in the visible spectrum. In normal daylight, about $1/10$ of the light energy is ultraviolet radiation. If the N3 center concentration is relatively high, for example, about 100 ppm, then visible blue light can be absorbed, and the diamond will exhibit a yellow color. This yellow color will lower the value of the diamond.

If the N3 center concentration is reduced, for example by treatment, so some yellow color-ing disappears, the remaining N3 centers can affect the brilliance of a diamond by a two-stage process. First, an ultraviolet photon is absorbed by an N3 center, and the energy is temporarily stored in the N3 center. Some of this stored energy leaks away as phonons or lattice vibrations. After a storage time pre-determined by the half-life of the N3 center, the N3 center may re-emit the remaining stored energy as light. Since some stored energy has been lost, the re-emitted light is not in the high-energy ultraviolet part of the spectrum. The re-emitted light now is in the visible part of the spectrum (this is known in the art as "ultraviolet downshifting").

The increased emission in the visible light spectrum is visible to humans, however the ultraviolet light is not visible to humans. Thus, the diamond may appear extraordinarily bright due to the increased visible light spectrum. Therefore, a controlled reduction of N3 centers concentration in a Type Ia diamond, by any appropriate treatment, may increase the value of a diamond. The diamond may increase in value by having N3 center concentration reduced so as to reduce or eliminate the yellow color in a diamond. Also, the remaining N3 centers will increase the brilliance of the diamond with respect to a Type IIa diamond, so as to increase the overall value of the diamond.

Previous attempts to treat diamonds, their results, and methods to detect the treatment processes will now be discussed to provide a further framework for the method, as embodied by the invention. Previous attempts to treat diamonds have not been generally successful, because in part to deleterious effects on the mechanical and optical properties and characteristics of the treated diamonds. For example, Lenzen reports in *Diamonds and Diamond Grading*, p. 207, Buttersworth, London (1983) that neutron and electron irradiation followed by annealing caused Type IIa diamonds to turn brown, thereby greatly lowering the diamond's value.

Diamonds that have been treated may exhibit altered mechanical and optical spectra signature properties and characteristics (hereinafter "optical spectra signature characteristics") . For example, treatment of greenish-yellow diamond by irradiation and heat-treating that resulted in altered optical spectra signature characteristics (also known as "detection signatures") was reported in *Gems & Gemology*, XXXIII, pp. 136–137, (Summer, 1997). According to this report, several treated round brilliant diamonds were given to the GIA for testing. The GIA determined that these diamonds had been treated, and inferred that the diamonds had been irradiated and subsequently heated to above 1450° C. The GIA also determined that normal irradiation signatures, such as a GR1 line at 741 nm and the HIb and HIc lines arising from a combination of irradiation and heat treatment were absent. The diamonds did exhibit a characteristic optical spectra signature absorption peak in the near infrared range at about 985 nm.

The altered optical spectra signature characteristics of treated diamonds may also be used to determine, analyze, evaluate, and detect if a diamond has been treated. It has been reported by J. Wilks, et al., *Properties and Applications of Diamonds*, p. 91, Buttersworth, London (1991) that diamonds without absorption peaks at 595 nm, 1936 nm, and 2024 nm, have "almost certainly not been treated".

Type Ia diamonds, in which N3 centers give a slight yellow color, have been commonly used diamonds for conventional irradiation and annealing treatments. Electron or neutron irradiation of Type Ia diamonds and a subsequent heat treatment generates H3 (Nitrogen-Vacancy-Nitrogen) centers and H4 (Nitrogen-Nitrogen-Vacancy-Nitrogen-Nitrogen) centers therein. These centers provide an amber gold color to the treated diamonds. The H3 centers and H4 Centers, respectively, have absorption bands at 503 nm and 496 nm, which are characteristic optical spectra signatures of these treated Type Ia diamonds. The ratios of H3 centers to H4 centers and the ratio of A centers to B centers can distinguish natural diamonds from irradiation and annealed treated diamonds. For example, in these treated diamonds, the following relationship exists:

$$H3/H4 = A/B$$

However, in natural diamonds, this ratio changes and becomes an inequality:

$$H3/H4 \gg A/B$$

These relations can be used with Type I diamonds to determine whether the diamonds have been treated, for example treated by irradiation and annealing. Some natural diamonds, for example Type II diamonds, have been found that may violate these general relations, because the naturally low nitrogen concentrations of Type II diamonds do not allow the measurement of the A center and B center concentrations.

A vacancy in a diamond can combine with a single nitrogen C Center to form an H2 Center (Nitrogen-Vacancy). The H2 Center can impart a distinguishable optical spectra signature characteristic to the treated diamonds. The H2 Center can cause a greenish color in the diamonds and its optical spectra signature characteristic is a vibronic absorption band at 637.3 nm. By absorbing light in the red at 637 nm, the remaining light coming from these treated diamonds is shifted towards a greenish color, and thus a detectable spectra signature characteristic for these diamonds is evident.

Approximately 10% of the daylight energy comprises ultraviolet energy (UV energy), which is invisible to the human eye. This UV energy can excite otherwise "invisible" color centers in the diamond and can cause them to luminance or fluoresce in the visible spectrum. Luminescence from color centers in diamonds can be suppressed by a high concentration of A Centers. If an A center is near a color center of a diamond, the UV energy that is absorbed by the color center will not re-radiate as fluorescence or photoluminescence. Rather, the UV energy that is absorbed by the diamond's color center will be transferred to the A Center, and undergo a non-radiative (invisible to humans) decay. A lattice vibration or, equivalently a phonon or heat, may be emitted from the diamond, rather than visible light, when an A Center is close to an excited color center that has absorbed UV light.

Therefore, if a greenish-yellow neon-like diamond color is desired, the concentration of A Centers is typically below a maximum concentration. Thus, all luminescence of the diamonds would be quenched, and an optical spectra signature characteristic will be evident. It has been determined that luminescence decreases with an increasing A Center concentration. For example, if 100% represents luminescence in the absence of A Centers, then about 100 ppm nitrogen in A Centers will decrease the luminescence by about 15%, while about 300 ppm nitrogen in A Centers will decrease the luminescence to only about 2.5%. It has been reported by G.Davies et al, Diamond Research 1978, 18–23 (1978) that if the nitrogen in A centers is less than about 50 ppm, the diamonds can still visibly luminance since sufficient UV energy-excited color centers are isolated from A centers. Therefore, excited color centers can re-radiate and luminance rather than undergo an invisible non-radiative decay.

Typical color centers in these diamonds that are excited by UV energy and UV light include the N3 Centers and H3 centers. A neon-like appearance of a diamond has been used as an optical spectra signature characteristic to illustrate that the diamond has been treated, or that the diamond's status with respect to treatment is indeterminable. Thus, this neon-like appearance is another optical spectra signature characteristic of treated diamonds.

Another process to alter a natural Type Ia diamond color comprises applications of high temperatures and pressures in a diamond-stable region, at which nitrogen atoms are mobile. It has been reported that mobility of nitrogen in diamond increases almost an order of magnitude for each about 100° C. increase in temperature by Evans, et al., *Proc Roy Soc Lond*, a 344, 111–130 (1975) and Bonzel, et al, *Proc Roy Soc Lond*, A 361, 109–127 (1978). These reports disclosed processing by annealing Type Ia diamonds, which may contain nitrogen, in the diamond stable region at temperatures above about 1960° C. under stabilizing pressures as high as about 85 kilobars (kbars) that are in a diamond stable region of the carbon Pressure-Temperature diagram (Carbon PT Diagram). Application of pressure was necessary to keep the diamond in the diamond-stable area of the Carbon PT Diagram. Otherwise, exposure of diamond to these high temperatures would result in the rapid graphitization on the diamond that is undesirable.

Most of the diamonds that have been treated by Evans and Bonzel were Type IaA/B diamonds comprising a mixture of platelets and nitrogen clusters, which may have been formed of either nitrogen pairs (A Centers) or quadruples (B Centers). In diamonds with predominantly A Center clusters, the diamonds turned a yellowish color as some of the clusters broke up and formed C Centers. Evans and Bonzel were apparently less successful in treating diamonds with predominantly B Centers, which may be more stable than A Centers. The most attractive and deepest yellow colors were obtained with Type Ia diamonds at temperatures in a range from about 2250° C. to about 2300° C. and under about 48 kilobars of pressure (Evans). This diamond treatment would also provide optical spectra signature characteristic of treated diamonds.

Although Evans achieved a successful color change, both the Type Ia and Type IIa diamonds lost some of their mechanical characteristics and properties, and crumbled into small pieces. The requirement to maintain the diamonds in the stable region of the carbon PT diagram necessitates extremely high pressures at the disclosed treatment temperatures. Such high pressures at the needed temperatures are generally difficult to attain and are not economical. Therefore, due to the constraints encountered, it is believed that diamond treatment has typically focused on irradiation and low-temperature annealing.

General Electric Company has announced that a process to improve diamond color of selected diamonds by exposing them to HPHT conditions typical of those in the earth's mantle may be possible. Many of these selected diamonds comprise Type I diamonds with low nitrogen concentrations or Type II diamonds comprising little, if any, nominal nitrogen. Conventional measurements of the A and B Center concentrations, H2, H3 and H4 center concentrations, optical and infrared spectral signatures associated with nitrogen, nitrogen complexes, vacancies and vacancy-nitrogen pairs, or vacancy-nitrogen-complex agglomerates in these selected diamonds have been difficult because of low concentration or lack of nitrogen therein. Accordingly, it has been difficult to determine whether the diamond has been processed, for example processed by exposure to a HPHT process. It has been determined that these GE processed diamonds may exhibit an optical spectra signature characteristic at 2.53 eV that is indicative of a nitrogen B center and vacancy.

In order to evaluate such HPHT processed diamonds, a method and system for detecting and determining these HPHT processed diamonds have been developed. The method, as embodied by the invention, will be discussed with respect to the detection system, and with respect to several non-limiting examples. A system 10 for detecting if a natural diamond has been processed is schematically illustrated in FIG. 1. The system 10 comprises a commercially available spectrometer 12 and an excitation and sample illumination laser 14. An example of the spectrometer 12, as embodied by the invention, comprises an ISA 750MP (MCD) Spectrometer made by Jobin-Yvon Spex Instruments, 3880 Park Ave, Edison, N.J., 08820 with a focal length=0.75 meter, an f/6 number with precision sine drive, a dispersion of 1.1 nm/mm, a resolution of 0.01 nm and an accuracy of 0.05 nm and with a Spectrum One CCD 1024×256 pixel detection liquid nitrogen detection array to decrease the time necessary to record a spectrum.

An exemplary excitation and sample illumination laser 14 comprises a 20-watt Spectra Physics Argon ion laser, with a Brewster prism of the laser adjusted to lase at the 4545 Angstrom line. The excitation and sample illumination laser 14 can be operated in a continuous wave (CW) mode. Alternative excitation and sample illumination lasers, within the scope of the invention, comprise an ultraviolet UV lasers, which are selected and tuned to maximize the photoluminescence of at least one of vacancies, nitrogen centers, nitrogen complexes, and vacancy-nitrogen complexes of interest in detecting HPHT processing of diamonds.

In FIG. 1, a diamond or diamond sample 16 is place in a cryostat 18 and cooled to a low temperature. The temperature can be that of liquid nitrogen temperature (100°K) or below. The excitation and sample illumination laser 14, which has been its Brewster-prism tuned to the 4545 argon ion line, is turned on to illuminate the cold diamond 16 in the cryostat 18. The ray 20 is directed through a window 22 to strike the diamond 16. The ray 20' then leaves the cryostat 18 through a window 24. A photoluminescent spectrum for the diamond 16 is then recorded in the spectrometer 12.

The spectrometer 12 is connected to a computer 26 so the photoluminescent spectrum of the illuminated diamond 16 is recorded. The computer 26 may comprise a monitor 28 that may in turn display the spectrum and optical spectra signature of the diamond 16.

The spectrum is examined for a line at 2.53 ev, which is believed to be related to the H4 line that is an emission line for a nitrogen B Center plus a vacancy. If the 2.53 eV line is present in the spectrum, the diamond 16 can be characterized as not having been through an HPHT process. If the 2.53 eV line is absent, the diamond has either been processed by an HPHT process, or contains an unusually low amount of nitrogen, such as less than 10 parts per billion of nitrogen. It is determined that the method, as embodied by the invention, provides the step of determining that the diamond was processed under HPHT conditions with up to about a 95% probability.

Other photoluminescent lines may also disappear during HPHT processing and can also be evaluated to determine if a diamond has been processed at HPHT. Even processed Type IIa diamonds, which are nominally free of nitrogen and have nitrogen in the parts per billion range, can be detected by the method, as embodied by the invention. With the advent of powerful ultraviolet lasers, virtually all Type IIa diamonds can be evaluated and HPHT processing can be detected by the method, as embodied by the invention, because these lasers may be capable of exciting suitable photoluminenscence lines with nitrogen as low as the parts per trillion range.

The following examples show how the invention can be practiced, but should not be construed as limiting. In this application, all units are in the metric system, unless otherwise stated. In the following non-limiting examples, processing of natural diamonds was done under high temperature and high pressure (HPHT) conditions using a belt type apparatus that is capable of reaching very high pressures, such as greater than about 30 kbars and high temperatures, such as greater than about 900° C. The spectrum are taken at an approximate temperature of liquid helium, about T=10°K.

EXAMPLE I

Figure 2:
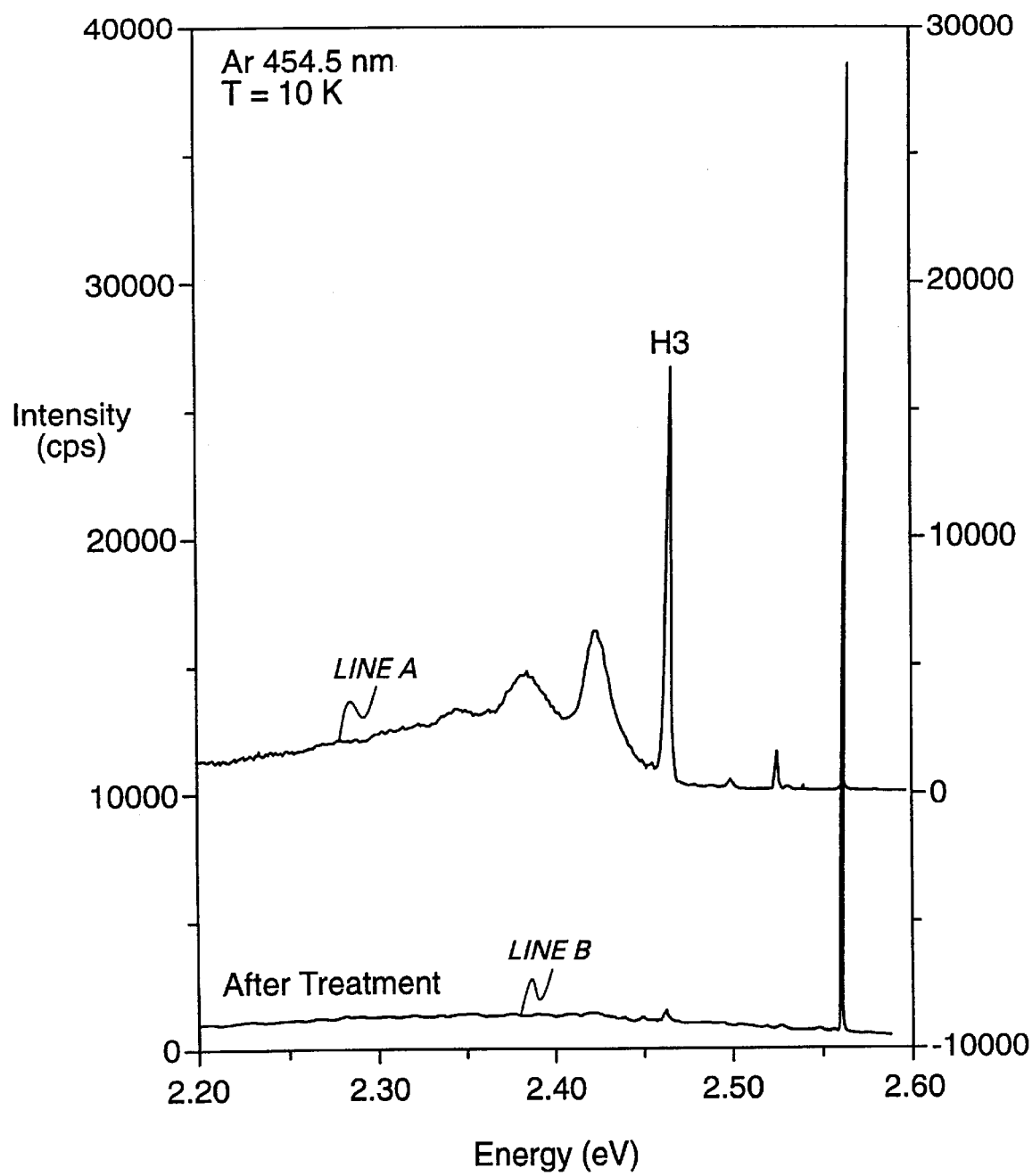
FIG. 2 is an illustration of spectra of a Type IIa diamond before and after high pressure and high temperature (HPHT) processing.

The spectrum of a brownish Type IIa diamond (0.53 carats) is taken before processing at liquid helium temperatures, and is illustrated by Line A in FIG. 2. The unprocessed Type IIa diamond has a distinct spectral line at 2.53 ev, which is an optical spectra signature characteristic. The diamond is then exposed to HPHT conditions of an HPHT process. The spectrum of this diamond, which is illustrated by Line B in FIG. 2, is again taken at liquid helium temperatures. The spectral line at 2.53 eV is not evident. The lack of a 2.53 eV spectral line in the processed diamond is a detection signature or optical spectra signature characteristic, showing that this diamond has been processed.

EXAMPLE II

Figure 3:
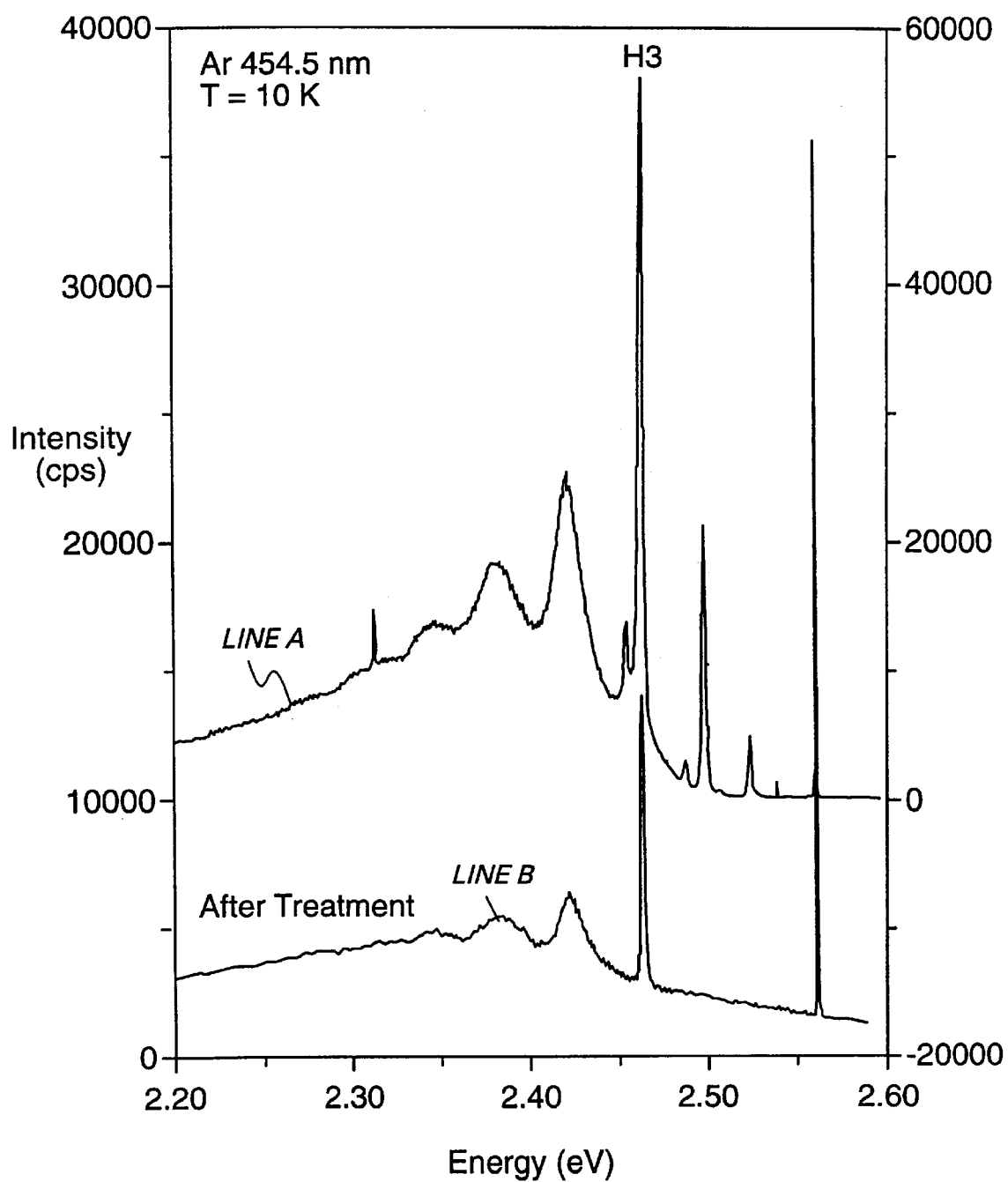
FIG. 3 is an illustration of spectra of a Type IaB diamond before and after HPHT processing.

The spectrum of a brownish Type IaB natural-rough diamond that contains about 1.3 ppm of nitrogen is taken at liquid helium temperatures before processing. This spectrum is illustrated as Line A in FIG. 3. This unprocessed diamond has a distinct spectral line at 2.53 eV. The diamond is then exposed to HPHT conditions of an HPHT process. The spectrum of this diamond is again taken at liquid helium temperatures, and is illustrated by Line B in FIG. 3. The spectral line at 2.53 eV has disappeared. The lack of a 2.53 eV spectral line in the processed diamond is a detection signature or optical spectra signature characteristic showing that this diamond has been processed. Spectral lines at 2.32, 2.34, 2.38, 2.42, 2.46, 2.49, 2.50 and 2.54 eV have also decreased significantly or disappeared during HPHT processing. These photoluminescence spectral lines may also be used as detection signatures showing that the diamond has been processed at HPHT.

EXAMPLE III

Figure 4:
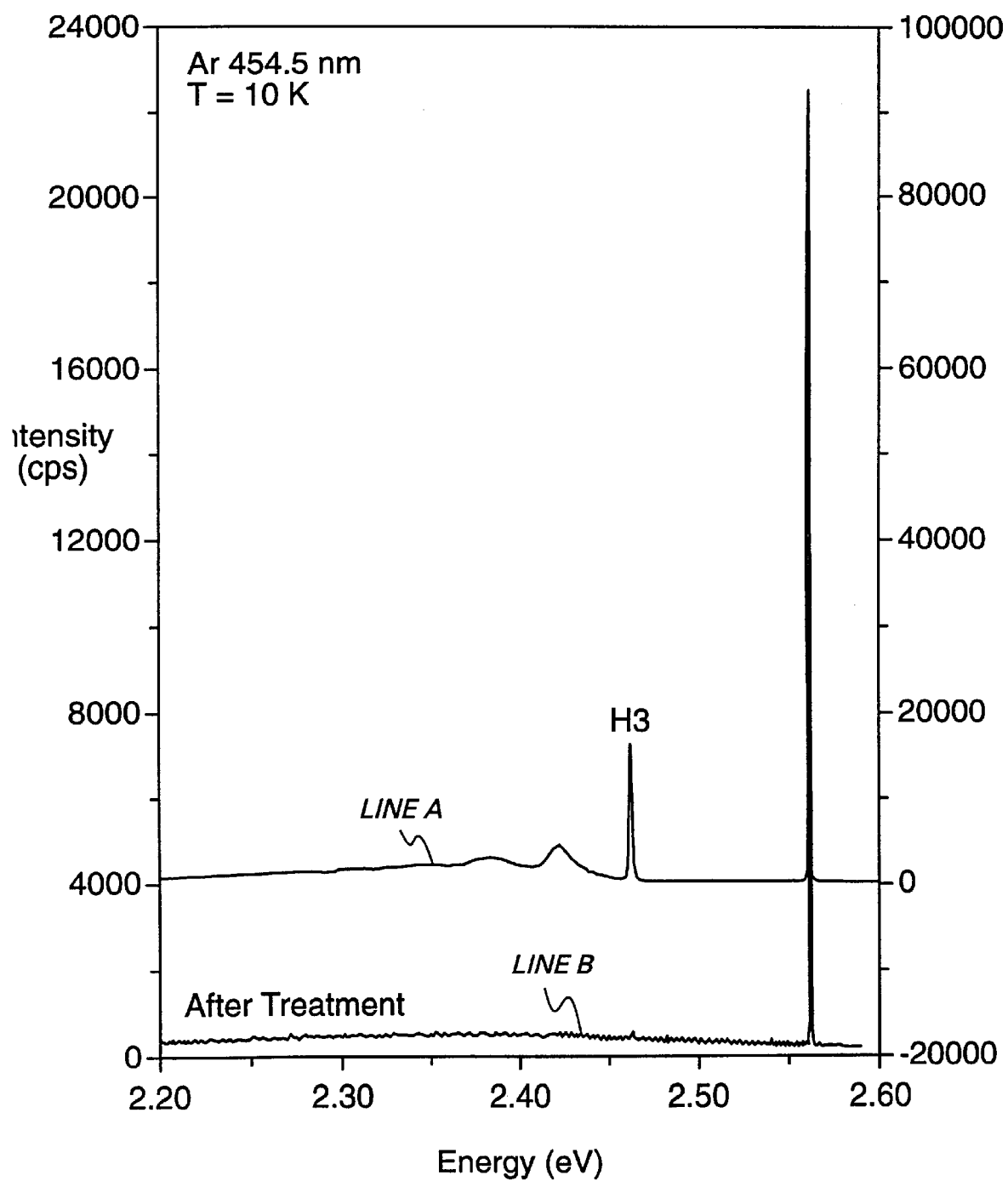
FIG. 4 is an illustration of spectra of a Type IIa diamond with extremely low nitrogen concentrations before and after HPHT processing.

The spectrum of an unusual Type IIa natural-rough diamond (0.65 carats) is taken at liquid helium temperatures before HPHT processing. This spectrum shows no spectral line at 2.53 eV, as evident in FIG. 4 (Line A). The spectral line may be missing because the diamond's nitrogen concentration is extremely low or because this diamond has seen some unusual HPHT conditions in nature that in essence mimic an HPHT process. The diamond is then exposed to the HPHT conditions of an HPHT process. The spectrum is again taken at liquid helium temperatures after processing, and is illustrated in FIG. 4 (Line B). The 2.53 eV spectral line is not in the spectrum. Also, the spectral line at 2.47 eV has decreased almost to the vanishing point. The detection method for an HPHT diamond may not be successful with natural diamonds of this type. However, it is believed that such diamonds amount to less than 5%.

EXAMPLE IV

The spectrum of a brownish Type IIb natural-rough diamond containing several parts per million of boron is taken at liquid helium temperatures before HPHT processing. This diamond does not show the typical boron spectral lines in the infrared region because the boron is apparently complexed with hydrogen making it IR inactive. This unprocessed diamond has a distinct spectral line at 2.53 eV due to some residual nitrogen in the diamond. The diamond is then exposed to the HPHT conditions of an HPHT process. The resulting diamond is medium blue in color, which indicates that the boron concentration exceeds the nitrogen concentration in the diamond by at least several parts per million. The spectrum of this diamond is again recorded at liquid helium temperatures. The spectral line at 2.53 eV has disappeared. The lack of a 2.53 eV spectral line is a detection signature showing that this diamond has been processed.

EXAMPLE V

The spectrum of a discolored pinkish Type IIa natural-rough diamond is taken at liquid helium temperatures before processing. This unprocessed diamond has a distinct spectral line at 2.53 eV due to residual nitrogen in the diamond. The diamond is then exposed to the HPHT conditions of an HPHT process. The resulting diamond is pinkish in color. The spectrum of this diamond is again recorded at liquid helium temperatures. The spectral line at 2.53 eV has disappeared. The lack of a 2.53 eV spectral line in the processed diamond is a detection signature showing that this diamond has been processed.

While various embodiments are described herein, it will be appreciated from the specification that various combinations of elements, variations or improvements therein may be made by those skilled in the art, and are within the scope of the invention.

We claim:

1. A method for detecting whether a natural diamond has been processed at high pressure and high temperature (HPHT) conditions, the method comprising:
   disposing a diamond in a cryostat that is provided at temperatures equal to or less than liquid nitrogen;
   illuminating the diamond with a laser beam;
   recording an optical spectrum of the diamond with a photoluminescence spectrometer; and
   examining the optical spectrum of the diamond to detect an absence of at least one selected photoluminescent spectral line,
   wherein if the at least one selected photoluminescent spectral line is not present in the optical spectrum, the method comprises determining that the diamond was processed under HPHT conditions, and wherein if the at least one selected photoluminescent spectral line is present in the optical spectrum, the method comprises determining that the diamond has not been subjected to HPHT conditions.

2. A method according to claim 1, further comprising the step of recovering the diamond.

3. A method according to claim 1, wherein the diamond comprises a Type IIa diamond.

4. A method according to claim 1, wherein the diamond comprises a colorless Type IIa diamond.

5. A method according to claim 1, wherein the diamond comprises a colorless Type Ia diamond.

6. A method according to clam 1, wherein the diamond comprises a pinkish Type IIa diamond.

7. A method according to claim 1, wherein the diamond comprises a blue Type IIb diamond.

8. A method according to claim 1, wherein the diamond comprises a yellow Type Ia diamond.

9. A method according to claim 1, wherein the diamond comprises at least one of a neon-like greenish yellow Type Ia, Type Ia/b, or Type Ib diamond.

10. A method according to claim 1, wherein the diamond comprises a green diamond.

11. A method according to claim 1, wherein the diamond comprises a chameleon diamond.

12. A method according to claim 1, wherein the diamond comprises at least one of a Type IaB ,Type IaA/B , Type IaA ,Type Ib, or Type Ia/b diamond.

13. A method according to claim 1, wherein the selected photoluminescence spectral line comprises a spectral line at 2.53 ev.

14. A method according to claim 1, wherein the selected photoluminescence spectral line comprises a spectral line at 2.38 ev.

15. A method according to claim 1, wherein the selected photoluminescence spectral line comprises a spectral line at 2.42 ev.

16. A method according to claim 1, wherein the selected photoluminescence spectral line comprises a spectral line at 2.46 ev.

17. A method according to claim 1, wherein the selected photoluminescence spectral line comprises a spectral line at 2.32 ev.

18. A method according to claim 1, wherein the selected photoluminescence spectral line comprises a spectral line at 2.45 ev.

19. A method according to claim 1, wherein the selected photoluminescence spectral line comprises a spectral line at 2.49 ev.

20. A method according to claim 1, wherein the selected photoluninescence spectral line comprises a spectral line at 2.50 ev.

21. A method according to claim 1, wherein the selected photoluminescence spectral line comprises a spectral line at 2.54 ev.

22. A method according to claim 1, wherein the selected photoluminescence spectral line comprises a spectral line in a range from about 1.30 eV to about 3.60 ev.

23. A method according to claim 1, wherein the step of examining comprises detecting if a 2.53 eV spectral line is present in the optical spectrum, wherein the presence of the 2.53 spectral line is an indication, with up to about a 95% probability, that the diamond was not processed under HPHT conditions.

24. A method according to claim 1, wherein the step of examining comprises detecting if a 2.53 eV spectral line is not present in the optical spectrum, wherein the absence of the 2.53 spectral line is an indication, with up to about a 95% probability, that the diamond has been subjected to HPHT conditions.

25. A method according to claim 1, wherein the step of illuminating comprises providing an argon-ion laser.

26. A method according to claim 25, wherein the step of illuminating comprises providing a laser that is tuned to maximize a photoluminescence spectral line used for detection of HPHT processing.

27. A method according to claim 26, wherein the step of illuminating comprises providing a laser with a Brewster-prism tuned to the 4545-Angstrom emission line.

28. A method according to claim 26, wherein the step of illuminating comprises providing a laser in which the power in a continuous wave mode is greater than about 2 watts.

29. A method according to claim 1, wherein the step of illuminating comprises providing an ultraviolet laser.

30. A method according to claim 29, wherein the step of illuminating comprises providing a laser that is tuned to maximize a photoluminescence spectral line used for detection of HPHT processing.

31. A system to perform the method according to claim 1, comprising:
   (a) the cryostat;
   (b) a laser; and
   (c) means for recording the selected photoluminescent spectral lines in the optical spectrum.

32. The method according to claim 1, wherein the diamond comprises a Type II diamond.

33. A method for predicting whether a natural diamond has been processed at high pressure and high temperature (HPHT) conditions, the method comprising:
   disposing a diamond in a cryostat that is provided at temperatures equal to or less than liquid nitrogen;
   illuminating the diamond with a laser beam,
   recording an optical spectrum of the diamond with a photoluminescence spectrometer;
   examining the optical spectrum of the diamond to detect an absence of at least one selected photoluminescent spectral line; and
   predicting that the diamond has been treated if the at least one selected photoluminescent spectral line is not in the optical spectrum,
   wherein if the at least one selected photoluminescent spectral line is not present in the optical spectrum, the method comprises determining that the diamond was processed under HPHT conditions, and wherein if the at least one selected photoluminescent spectral line is present in the optical spectrum, the method comprises determining that the diamond has not been subjected to HPHT conditions.

34. A method according to claim 33, further comprising the step of recovering the diamond.

35. A method according to claim 33, wherein the diamond comprises a Type IIa diamond.

36. A method according to claim 33, wherein the diamond comprises a colorless Type IIa diamond.

37. A method according to claim 33, wherein the diamond comprises a colorless Type Ia diamond.

38. A method according to claim 33, wherein the diamond comprises a pinkish Type IIa diamond.

39. A method according to claim 33, wherein the diamond comprises a blue Type IIb diamond.

40. A method according to claim 33, wherein the diamond comprises a yellow Type Ia diamond.

41. A method according to claim 33, wherein the diamond comprises at least one of a neon-like greenish yellow Type Ia , Type Ib, or Type Ib diamond.

42. A method according to claim 33, wherein the diamond comprises a green diamond.

43. A method according to claim 33, wherein the diamond comprises a chameleon diamond.

44. A method according to claim 33, wherein the diamond comprises at least one of a Type IaB ,Type IaA/B , Type IaA ,Type Ib, or Type Ia/b diamond.

45. A method according to claim 33, wherein the selected photoluminescence spectral line comprises a spectral line at 2.53 ev.

46. A method according to claim 33, wherein the selected photoluminescence spectral line comprises a spectral line at 2.38 ev.

47. A method according to claim 33, wherein the selected photoluminescence spectral line comprises a spectral line at 2.42 ev.

48. A method according to claim 33, wherein the selected photoluminescence spectral line comprises a spectral line at 2.46 ev.

49. A method according to claim 33, wherein the selected photoluminescence spectral line comprises a spectral line at 2.32 ev.

50. A method according to claim 33, wherein the selected photoluminescence spectral line comprises a spectral line at 2.45 ev.

51. A method according to claim 33, wherein the selected photoluminescence spectral line comprises a spectral line at 2.49 ev.

52. A method according to claim 33, wherein the selected photoluminescence spectral line comprises a spectral line at 2.50 ev.

53. A method according to claim 33, wherein the selected photoluminescence spectral line comprises a spectral line at 2.54 ev.

54. A method according to claim 33, wherein the selected photoluminescence spectral line comprises a spectral line in a range from about 1.30 eV to about 3.60 ev.

55. A method according to claim 33,wherein the steps of examining and predicting comprise examining the optical spectrum for detecting if a 2.53 eV spectral line is not present, and if the 2.53 eV spectral line is not present in the optical spectrum, the step of predicting comprises determining with up to about a 95% probability that the diamond was processed under HPHT conditions.

56. A method according to claim 33, wherein the steps of examining and predicting comprise examining the optical spectrum for detecting if a 2.53 eV spectral line is present, and if the 2.53 eV spectral line is present, the step of predicting comprises determining that the diamond has not been subjected to HPHT conditions.

57. A method according to claim 33, wherein the step of illuminating comprises providing an argon-ion laser.

58. A method according to claim 57, wherein the step of illuminating comprises providing a laser that is tuned to maximize a photoluminescence spectral line used for detection of HPHT processing.

59. A method according to claim 57, wherein the step of illuminating comprises providing an ultraviolet laser.

60. A method according to claim 59, wherein the step of illuminating comprises providing a laser that is tuned to maximize a photoluminescence spectral line used for detection of HPHT processing.

61. A method according to claim 57, wherein the step of illuminating comprises providing a laser with a Brewster-prism tuned to the 4545-Angstrom emission line.

62. A method according to claim 57, wherein the step of illuminating comprises providing a laser in which the power in a continuous wave mode is greater than about 2 watts.

63. A system to perform the method according to claim 1, comprising:
   (a) the cryostat;
   (b) a laser; and
   (c) means for recording the selected photoluminescent spectral lines in the optical spectrum.

64. A method for detecting whether a natural diamond has been processed at high pressure and high temperature (HPHT) conditions, the method comprising:
   disposing a diamond in a cyrostat that is provided at temperatures equal to or less than liquid nitrogen;
   illuminating the diamond with a laser beam;
   recording an optical spectrum of the diamond with a photoluminescence spectrometer; and
   examining the optical spectrum of the diamond to detect an absence of a photoluminescent spectral line at 2.53 eV,
   wherein if the 2.53 eV spectral line is not present in the optical spectrum, the method comprises determining with up to about a 95% probability exists that the diamond was processed under HPHT conditions, and if the 2.53 eV spectral line is present, the method comprises determining that the diamond has not been subjected to HPHT conditions.

65. A system to perform the method according to claim 64, comprising:
   (a) the cryostat;
   (b) a laser; and
   (c) means for recording the photoluminescent spectral line in the optical spectrum.

66. The system of claim 65, wherein element (c) comprises a photoluminescence spectrometer.

67. A method for predicting whether a natural diamond has been processed at high pressure and high temperature (HPHT) conditions, the method comprising:
   disposing a diamond in a cyrostat that is provided at temperatures equal to or less than liquid nitrogen;
   illuminating the diamond with a laser beam;
   recording an optical spectrum of the diamond with a photoluninescence spectrometer;
   examining the optical spectrum of the diamond to detect an absence of a photoluminescent spectral line at 2.53 eV; and predicting that the diamond has been treated if photoluminescent spectral line at 2.53 eV is not evident in the optical spectrum, wherein if the 2.53 eV spectral line is not present in the optical spectrum, the method comprises determining with up to about a 95% probability exists that the diamond was processed under HPHT conditions, and if the 2.53 eV spectral line is present in the optical spectrum, the method comprises determining that the diamond has not been subjected to HPHT conditions.

68. A system to perform the method according to claim 67, comprising:
   (a) the cryostat;
   (b) a laser; and
   (c) means for recording the photoluminescent spectral line in the optical spectrum.

69. The system of claim 68, wherein element (c) comprises a photoluminescence spectrometer.

* * * * *